US008728163B2

(12) United States Patent
Theofilos et al.

(10) Patent No.: US 8,728,163 B2
(45) Date of Patent: May 20, 2014

(54) ARTIFICIAL DISC REPLACEMENT DEVICE (75) Inventors: Charles Theofilos, Palm Beach Gardens, FL (US); George England, Boynton Beach, FL (US)

(73) Assignee: K2M, Inc., Leesburg, VA (US)

( * ) Notice: Subject to any disclaimer, the term of this patent is extended or adjusted under 35 U.S.C. 154(b) by 0 days.

(21) Appl. No.: 13/455,225

(22) Filed: Apr. 25, 2012

(65) Prior Publication Data
US 2012/0209389 A1 Aug. 16, 2012

Related U.S. Application Data (63) Continuation of application No. 12/408,100, filed on Mar. 20, 2009, now abandoned.

(60) Provisional application No. 61/070,126, filed on Mar. 20, 2008.

(51) Int. Cl.
*A61F 2/44* (2006.01)

(52) U.S. Cl.
USPC ..... 623/17.15; 606/246; 606/279; 623/17.14; 623/17.16

(58) Field of Classification Search
USPC ........................................... 623/17.11–17.16
See application file for complete search history.

(56) References Cited

U.S. PATENT DOCUMENTS

| 4,759,766 | A | * | 7/1988 | Buettner-Janz et al. | ... 623/17.15 |
| 4,997,432 | A | * | 3/1991 | Keller | ........................ 623/17.11 |
| 5,258,031 | A | * | 11/1993 | Salib et al. | ................. 623/17.15 |
| 5,306,308 | A | | 4/1994 | Gross et al. | |
| 5,314,477 | A | * | 5/1994 | Marnay | ...................... 623/17.15 |
| 5,370,697 | A | | 12/1994 | Baumgartner | |
| 5,401,269 | A | | 3/1995 | Büttner-Janz et al. | |
| 5,425,773 | A | * | 6/1995 | Boyd et al. | ................. 623/17.15 |
| 5,458,642 | A | | 10/1995 | Beer et al. | |
| 5,507,816 | A | | 4/1996 | Bullivant | |
| 5,534,029 | A | | 7/1996 | Shima | |
| 5,556,431 | A | | 9/1996 | Büttner-Janz | |
| 5,676,701 | A | | 10/1997 | Yuan et al. | |
| 5,676,702 | A | | 10/1997 | Ratron | |
| 5,893,889 | A | | 4/1999 | Harrington | |
| 5,989,291 | A | | 11/1999 | Ralph et al. | |
| 6,228,118 | B1 | | 5/2001 | Gordon | |
| 6,231,609 | B1 | | 5/2001 | Mehdizadeh | |
| 6,368,350 | B1 | | 4/2002 | Erickson et al. | |
| 6,375,682 | B1 | | 4/2002 | Fleischmann et al. | |
| 6,395,035 | B2 | | 5/2002 | Bresina et al. | |
| 6,402,785 | B1 | | 6/2002 | Zdeblick et al. | |
| 6,517,580 | B1 | | 2/2003 | Ramadan et al. | |
| 6,527,804 | B1 | | 3/2003 | Gauchet et al. | |
| 6,582,468 | B1 | | 6/2003 | Gauchet | |
| 6,607,558 | B2 | | 8/2003 | Kuras | |
| 6,626,943 | B2 | | 9/2003 | Eberlein et al. | |
| 6,682,562 | B2 | | 1/2004 | Viart et al. | |
| 6,706,068 | B2 | | 3/2004 | Ferree | |
| 6,723,127 | B2 | | 4/2004 | Ralph et al. | |

(Continued)

*Primary Examiner* — Jerry Cumberledge
(74) *Attorney, Agent, or Firm* — Carter, DeLuca, Farrell & Schmidt, LLP (57) ABSTRACT

An artificial disk replacement device includes opposing plate members with a pivoting assembly disposed therebetween. The pivoting assembly allows the plate members to pivot relative to each other in a first direction, but inhibit movement of the plate members in a second direction. The plate members may be installed prior to installing the pivoting assembly. An installation tool for use with the artificial disk replacement device is also disclosed.

28 Claims, 8 Drawing Sheets

(56) References Cited

U.S. PATENT DOCUMENTS

| | | | |
|---|---|---|---|
| 6,726,720 B2 | 4/2004 | Ross et al. | |
| 6,733,532 B1 | 5/2004 | Gauchet et al. | |
| 6,740,118 B2 | 5/2004 | Eisermann et al. | |
| 6,793,678 B2 | 9/2004 | Hawkins | |
| 6,875,235 B2 | 4/2005 | Ferree | |
| 6,936,071 B1 | 8/2005 | Marnay et al. | |
| 6,981,989 B1 * | 1/2006 | Fleischmann et al. | 623/17.11 |
| 6,986,789 B2 | 1/2006 | Schultz et al. | |
| 6,994,727 B2 | 2/2006 | Khandkar et al. | |
| 7,001,432 B2 | 2/2006 | Keller et al. | |
| 7,001,433 B2 | 2/2006 | Songer et al. | |
| 7,025,787 B2 | 4/2006 | Bryan et al. | |
| 7,048,766 B2 | 5/2006 | Ferree | |
| 7,105,024 B2 | 9/2006 | Richelsoph | |
| 7,128,761 B2 | 10/2006 | Kuras et al. | |
| 7,156,876 B2 | 1/2007 | Moumene et al. | |
| 7,198,644 B2 | 4/2007 | Schultz et al. | |
| 7,204,852 B2 | 4/2007 | Marnay et al. | |
| 7,255,714 B2 | 8/2007 | Malek | |
| 7,270,679 B2 | 9/2007 | Istephanous et al. | |
| 7,282,063 B2 | 10/2007 | Cohen et al. | |
| 7,331,994 B2 | 2/2008 | Gordon et al. | |
| RE40,260 E | 4/2008 | Bühler | |
| 7,361,192 B2 | 4/2008 | Doty | |
| 7,402,176 B2 * | 7/2008 | Malek | 623/17.16 |
| 7,485,146 B1 * | 2/2009 | Crook et al. | 623/17.15 |
| 7,491,241 B2 | 2/2009 | Errico et al. | |
| 7,517,363 B2 | 4/2009 | Rogers et al. | |
| 7,563,286 B2 * | 7/2009 | Gerber et al. | 623/17.14 |
| 7,771,481 B2 * | 8/2010 | Khandkar et al. | 623/17.15 |
| 7,909,877 B2 * | 3/2011 | Krueger et al. | 623/17.15 |
| 7,927,374 B2 * | 4/2011 | Duggal et al. | 623/17.14 |
| 8,172,904 B2 * | 5/2012 | Duggal et al. | 623/17.15 |
| 2002/0128715 A1 | 9/2002 | Bryan et al. | |
| 2003/0045939 A1 | 3/2003 | Casutt | |
| 2003/0069643 A1 | 4/2003 | Ralph et al. | |
| 2004/0002761 A1 | 1/2004 | Rogers et al. | |
| 2004/0133281 A1 * | 7/2004 | Khandkar et al. | 623/17.16 |
| 2004/0138750 A1 | 7/2004 | Mitchell | |
| 2004/0143332 A1 * | 7/2004 | Krueger et al. | 623/17.14 |
| 2004/0172135 A1 * | 9/2004 | Mitchell | 623/17.15 |
| 2004/0220668 A1 | 11/2004 | Eisermann et al. | |
| 2005/0159818 A1 * | 7/2005 | Blain | 623/17.15 |
| 2005/0267581 A1 | 12/2005 | Marnay et al. | |
| 2006/0020341 A1 | 1/2006 | Schneid et al. | |
| 2006/0122703 A1 * | 6/2006 | Aebi et al. | 623/17.15 |
| 2008/0109081 A1 | 5/2008 | Bao et al. | |
| 2009/0062920 A1 | 3/2009 | Tauber | |
| 2009/0082867 A1 | 3/2009 | Bueno et al. | |
| 2009/0132052 A1 | 5/2009 | Baccelli et al. | |
| 2010/0057205 A1 * | 3/2010 | Justin et al. | 623/17.15 |

* cited by examiner

ARTIFICIAL DISC REPLACEMENT DEVICE

CROSS-REFERENCE TO RELATED APPLICATIONS

This application is a continuation of U.S. patent application Ser. No. 12/408,100, filed Mar. 20, 2009, which claims priority to, and the benefit of, U.S. Provisional Patent Application Ser. No. 61/070,126, filed Mar. 20, 2008, the entire contents of which are hereby incorporated by reference.

BACKGROUND

1. Technical Field

This application relates to a device for use in orthopedic spine surgery. In particular, the present invention relates to an artificial disc replacement device that replaces a damaged or diseased intervertebral disc.

2. Background of Related Art

The human spine is composed of thirty-three vertebrae at birth and twenty-four as a mature adult. Between each pair of vertebrae is an intervertebral disc, which maintains the space between adjacent vertebrae and acts as a cushion under compressive, bending, and rotational loads and motions. A healthy intervertebral disc has a great deal of water in the nucleus pulposus, which is the center portion of the disc. The water content gives the nucleus a spongy quality and allows it to absorb spinal stress. Excessive pressure or injuries to the nucleus can cause injury to the annulus, which is the outer ring that holds the disc together. Generally, the annulus is the first portion of the disc that experiences injury. These injuries are typically in the form of small tears. These tears heal by scar tissue. The scar tissue is not as strong as normal annulus tissue. Over time, as more scar tissue forms, the annulus becomes weaker. Eventually this can lead to damage of the nucleus pulposus. The nucleus begins to lose its water content due to the damage; it begins to dry up. Because of water loss, the discs lose some of their ability to act as a cushion. This can lead to even more stress on the annulus and still more tears as the cycle repeats. As the nucleus loses its water content, it collapses, allowing the vertebrae above and below the disc space to move closer to one another. This results in a narrowing of the disc space between the two vertebrae. As this shift occurs, the facet joints located at the back of the spine are forced to shift. This shift changes the way the facet joints work together and can cause problems in the facet joints as well.

When a disc or vertebrae is damaged due to disease or injury, standard practice is to remove all or part of the intervertebral disc, insert a natural or artificial disc spacer, and construct an artificial structure to hold the affected vertebrae in place to achieve a spinal fusion. In doing so, while the diseased or injured anatomy is addressed and the accompanying pain is significantly reduced, the natural biomechanics of the spine are affected in a unique and unpredictable way. More often than not, the patient will develop complicating spinal issues in the future.

To that end, there is an overall need to treat the disease or injury while maintaining or preserving the natural spine biomechanics. Normal spine anatomy, specifically intervertebral disc anatomy, allows one vertebra to rotate with respect to its adjacent vertebra about all three axes. Similarly, the intervertebral disc also allows adjacent vertebra to translate along all three axes with respect to one another.

For the above stated reasons, a need exits for an implantable device which may be used as an artificial disc replacement thereby maintaining disc height and motion. More specifically, the motion maintained must address at least the principle motions of rotation about all three axes. The device must also have a means to inhibit or minimize expulsion of the device from its installed location. The implantable device has an additional need of having a prolonged life span in the body that can withstand early implantation, as is often indicated for younger patients. In addition, the implantable device will have a limited amount of particulate debris so as to reduce complications over the useful life of the device.

SUMMARY

The present disclosure relates to an artificial disk replacement device or disk. The disk includes opposing plate members with a pivoting assembly disposed therebetween. The pivoting assembly may include a support member and a cup. Additionally, the pivoting assembly may include an engagement member. The pivoting assembly is configured for slidable insertion into openings in the first and second plate members. Each plate member may include one or more teeth for securely engaging endplates of adjacent vertebral bodies.

The pivoting assembly is adapted for allowing relative movement of the first and second plate members with respect to each other in a first direction, while inhibiting relative movement of the first and second plate members in a second direction. The first direction is transverse or orthogonal with respect to the first direction.

One embodiment of the disk is adapted for use in lumbar procedures. In this embodiment, the support member includes a hemispherical dome with opposing arms that lie in the first direction. The cup has opposing openings adapted for pivotally engaging the arms of the support member. As such, the cup moves symmetrically about the axis extending through the arms and the openings.

In an alternate embodiment, the disk is adapted for use in cervical procedures. In this embodiment, the dome of the support member is eccentric or asymmetric with respect to the axis extending through the opposing arms. Thus, when the cup pivots about the axis extending through the arms, the asymmetric configuration of the dome interacts with the cup causing the plate members of the disk to pivot and lift (i.e. increase the distance between the plate members).

An installation tool and a method of installing the disk are also disclosed. The installation tool has a handle, a knob, and a shaft. At the distal end of the installation tool, a pair of opposing jaws or blade portions exists. The blade portions releasably engage the first and second plate members. An attachment portion is located at a distal end of the shaft for releasably engaging the pivoting assembly of the disk. With the first and second plate members attached to the blade portions and the pivoting assembly coupled to the attachment portion, the physician inserts the distal end of the installation tool between the adjacent vertebral bodies. Rotating the handle in one direction causes the shaft to translate distally through the installation tool. As the pivoting assembly moves distally, it engages inner surfaces of the blade portions urging them apart. Once the pivoting assembly is fully translated in the distal direction, the support member and the engagement member slide into openings in the respective first and second plate members, thereby securing the pivoting assembly between the first and second plate members and completing the assembly of the disk. Since the distraction of the adjacent vertebral bodies is performed prior to installing the pivoting assembly, this reduces the installation force necessary to install the disk. Thus, the potential trauma to the patient is reduced and any possibility of deforming the disk is also reduced.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION OF EMBODIMENTS

Particular embodiments of the present disclosure will be described herein with reference to the accompanying drawings. In the drawings and in the description that follows, the term "proximal," will refer to the end of a device or system that is closest to the operator, while the term "distal" will refer to the end of the device or system that is farthest from the operator. In addition, the term "cephalad" is used in this application to indicate a direction toward a patient's head, whereas the term "caudad" indicates a direction toward the patient's feet. Further still, for the purposes of this application, the term "medial" indicates a direction toward the middle of the body of the patient, whilst the term "lateral" indicates a direction toward a side of the body of the patient (i.e., away from the middle of the body of the patient). The term "posterior" indicates a direction toward the patient's back, and the term "anterior" indicates a direction toward the patient's front.

Figure 1:
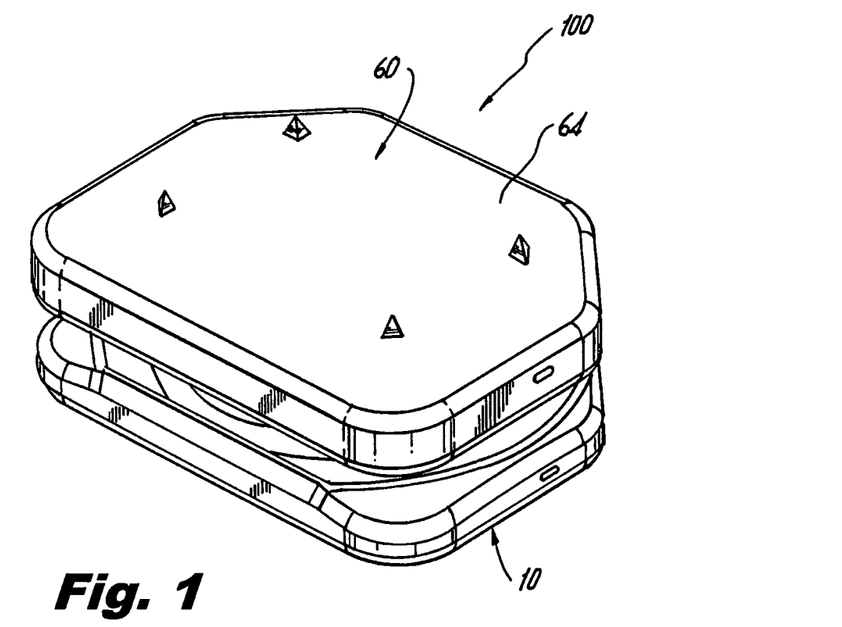
FIG. 1 is a perspective view of the presently disclosed artificial disc replacement device.
Figure 2:
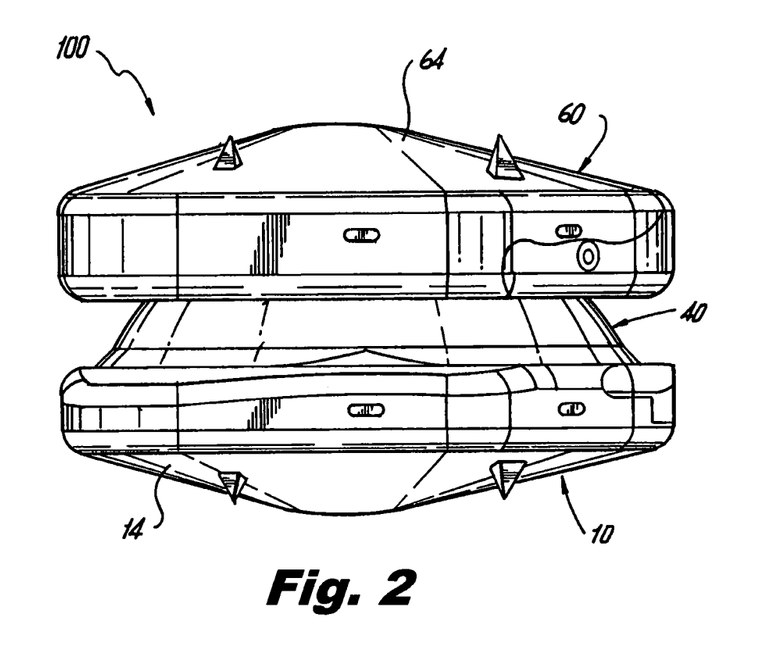
FIG. 2 is an end view of the artificial disc replacement device of FIG. 1.
Figure 3:
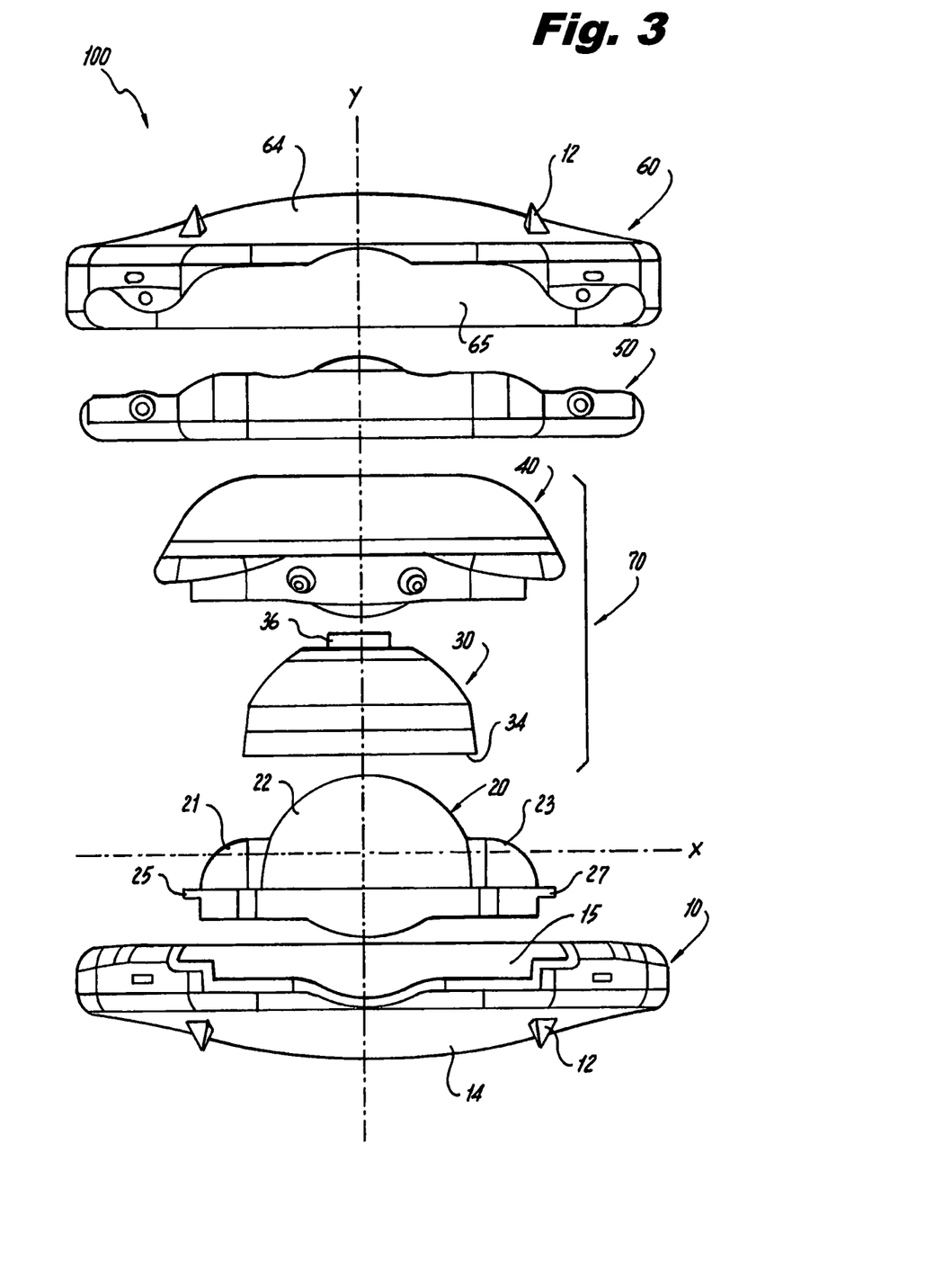
FIG. 3 is an exploded side view, with parts separated, of the artificial disc replacement device of FIG. 1.
Figure 4:
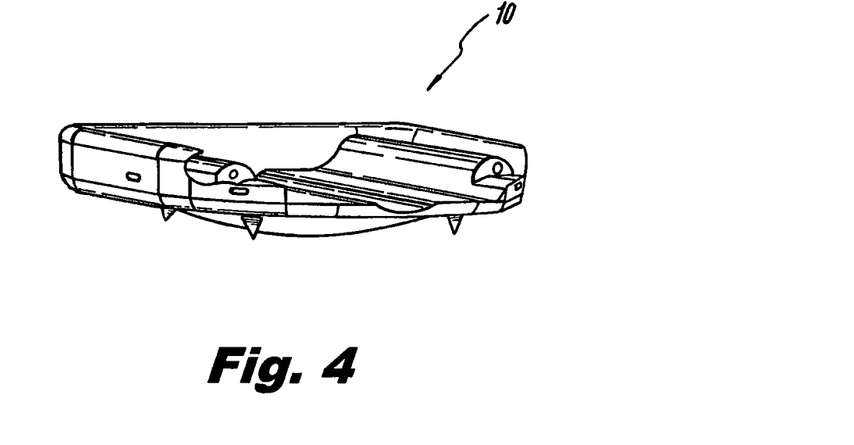
FIG. 4 is a perspective view of a first plate member of the artificial disc replacement device of FIG. 1.

Referring now to the drawings, in which like reference numerals identify identical or substantially similar parts throughout the several views, FIGS. 1-3 illustrate an embodiment of the presently disclosed artificial disk replacement device or disk 100. Disk 100 includes a first plate member 10, a support member 20, a cup 30, a coupling member 40, an engaging member 50, and a second plate member 60.

Each of the first and second plate members 10, 60 have a superior surface adapted for engaging an endplate of a vertebral body. One or more teeth 12 are disposed on the superior surface 14, 64 of the first and second plate members 10, 60. Each tooth 12 has a generally pyramidal configuration for securely engaging the endplate of the respective vertebral body. It is contemplated that each tooth 12 may have other configurations that are configured and dimensioned for securely engaging the vertebral endplate. The superior surfaces 14, 64 are curvate surfaces, although other configurations are contemplated. In addition, each plate member 10, 60 includes an opening 15, 65 along one side thereof.

Figures 8, 9A:
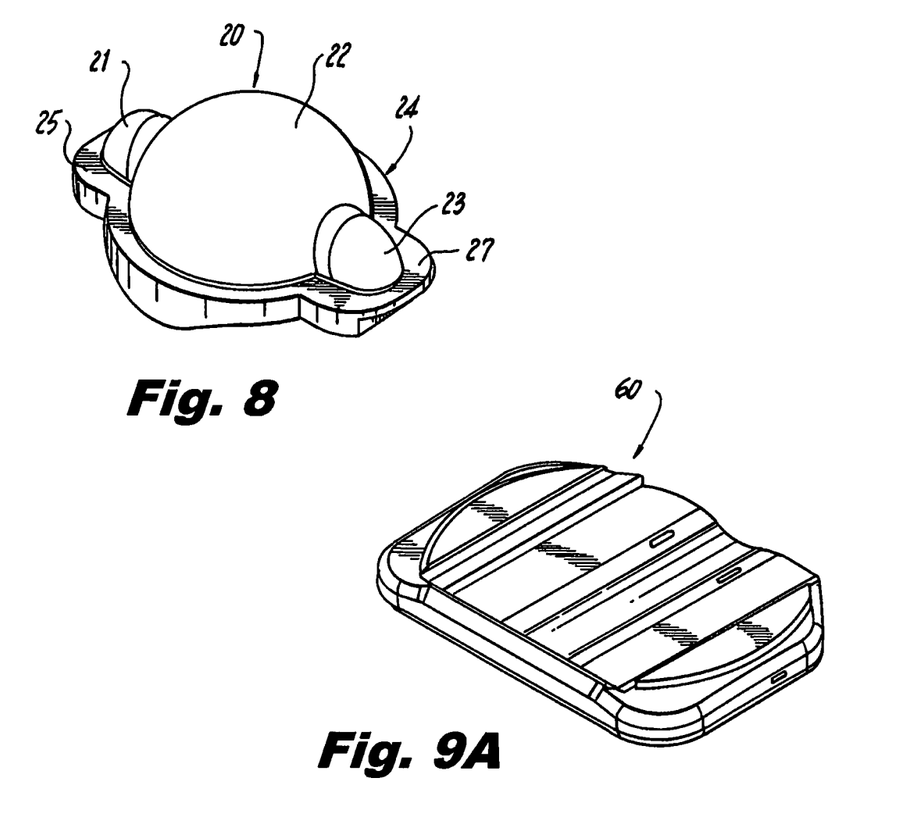
FIG. 8 is a perspective view of a support member of the artificial disc replacement device of FIG. 1.
FIG. 9A is a perspective view of a second plate member of the artificial disc replacement device of FIG. 1.
Figure 9B:
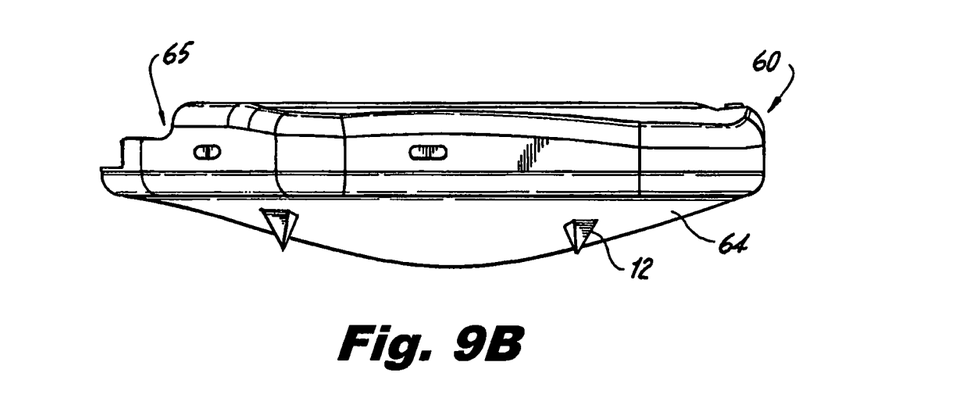
FIG. 9B is an end view of the second plate member of the artificial disc replacement device of FIG. 1.

With reference to FIGS. 3 and 8, the support member 20 includes a dome 22 disposed on a base portion 24. The dome 22 has a generally spherical shape. The support member 20 includes opposing arms 21, 23 that are positioned on wing portions 25, 27 of the base portion 24. The wing portions 25, 27 are adapted for slidable engagement with the opening 15 of the first plate member 10 (FIG. 3). After the support member 20 is inserted into the opening 15, the first plate member 10 and the support member 20 are securely affixed to one another. Alternatively, the dome 22 may have an alternate configuration such that it is somewhat asymmetrical or eccentric.

Figure 6:
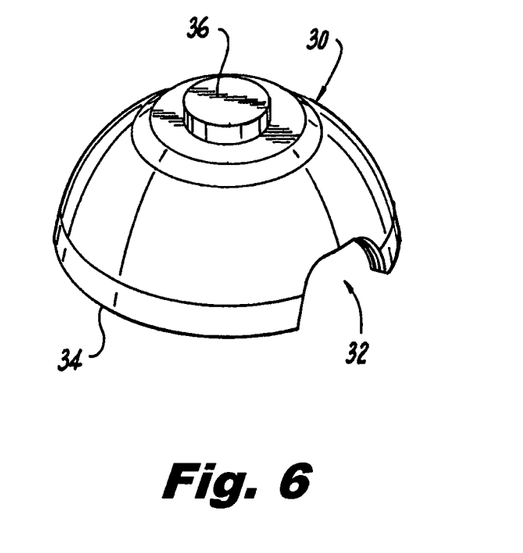
FIG. 6 is a perspective view of a cup of the artificial disc replacement device of FIG. 1.

Referring now to FIGS. 3 and 6, the cup 30 is a generally hemispherical structure with a pair of opposed openings. Although only one opening 32 is shown, the opposing opening is substantially similar to the opening 32. Each opening 32 is configured and dimensioned for slidable engagement with the arms 21, 23. The cup 30 has a configuration that is complementary to that of the dome 22. In one embodiment, the dome 22 is generally hemispherical and the cup 30 has a complementary configuration. As such, the cup 30 nests atop the support member 20 such that the openings 32 rest atop the arms 21, 23. The cup 30 and the dome 22 are configured such that a gap is defined between a bottom lip 34 of the cup 30 and the base portion 24 of the support member 20. This permits the cup 30 to pivot about an axis X of the disk 100. An extension 36 is disposed on one end of the cup 30 opposite to the bottom lip 34.

Figure 7:
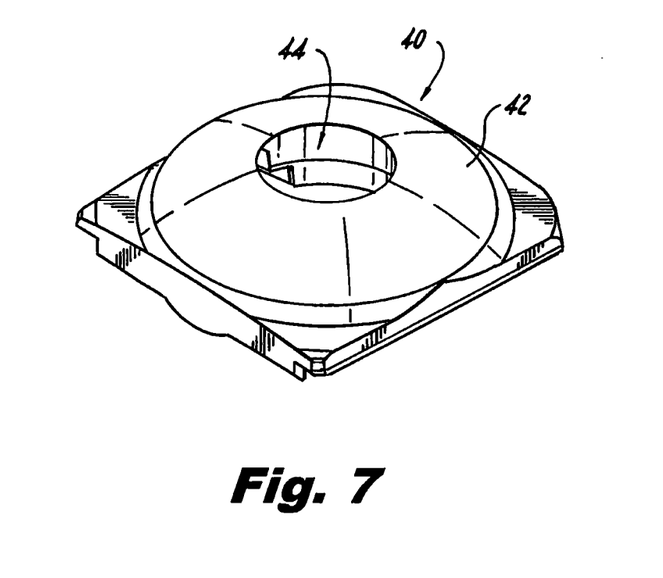
FIG. 7 is a perspective view of an articulating insert of the artificial disc replacement device of FIG. 1.

The coupling member 40 (FIGS. 3 and 7) has a curvate upper surface 42 and a central opening 44. The opening 44 is configured for receiving the extension 36 of the cup 30. When the coupling member 40 is coupled to the cup 30, the opening 44 receives the extension 36.

Figure 5:
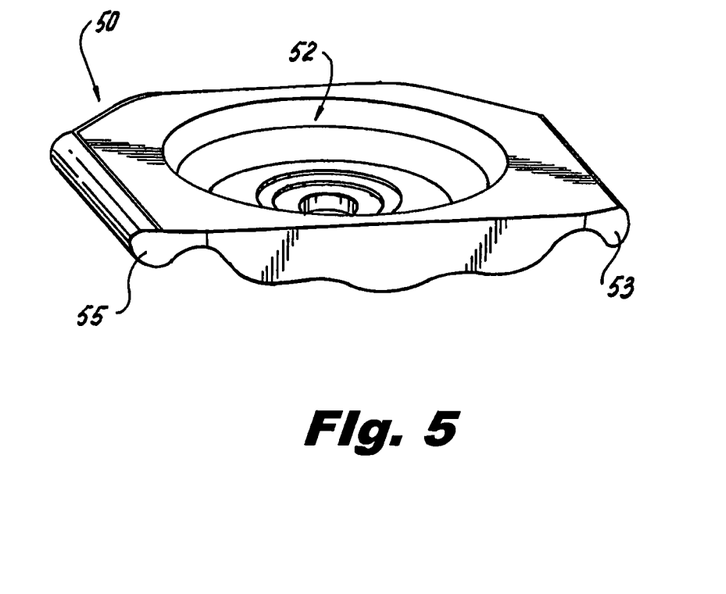
FIG. 5 is a perspective view of an insert of the artificial disc replacement device of FIG. 1.

The engaging member 50 (FIGS. 3 and 5) includes a recess 52 and wings 53, 55. The wings 53, 55 are configured for slidably engaging the recess 65 of the second plate member 60. After sliding the engaging member 50 into the second plate member 60, the engaging member 50 is securely affixed to the second plate member 60.

The disk 100 may be considered as the first and second plate members 10, 60 having a pivoting assembly 70 (FIG. 3) disposed therebetween. The pivoting assembly 70 includes the support member 20 and the cup 30. The pivoting assembly 70 may include the coupling member 40 in one of its embodiments. As assembled, the pivoting assembly 70 permits movement of the first and second plate members 10, 60 with respect to the axis X (FIG. 3), while inhibiting movement of the first and second plate members 10, 60 with respect to axis Y (FIG. 3). As such, the first and second plate members 10, 60 are capable of pivoting in a first direction and are inhibited from pivoting in a second direction, wherein the second direction is transverse or orthogonal to the first direction. This arrangement permits a predetermined range of movement of the adjacent vertebral bodies, while simultaneously inhibiting rotational movement of the adjacent vertebral bodies.

The presently disclosed disk 100 is suitable for use in cervical applications as well as in lumbar applications. When used in cervical applications, the dome 22 of the support member 20 (FIG. 8) has an eccentric or asymmetrical configuration. Coupling this with the cup 30 having a complementary configuration, allows the disk to pivot about the axis X, and provides a desired amount of lift. As used herein, the term lift refers to displacement of the first and second plate members 10, 60 with respect to each other along the axis Y. As such, pivoting the first and second plate members 10, 60 about the axis X, also causes the first and second plate members 10, 60 to move away from each other along the axis Y, thereby defining the lift of the disk 100. In lumbar applications, the dome 22 of the support member 20 is generally hemispherical and the cup has a complementary configuration. This arrangement allows the first and second plate members 10, 60 to pivot about the axis X without the first and second plate members 10, 60 moving relative to each other along the axis Y.

Figure 10A:
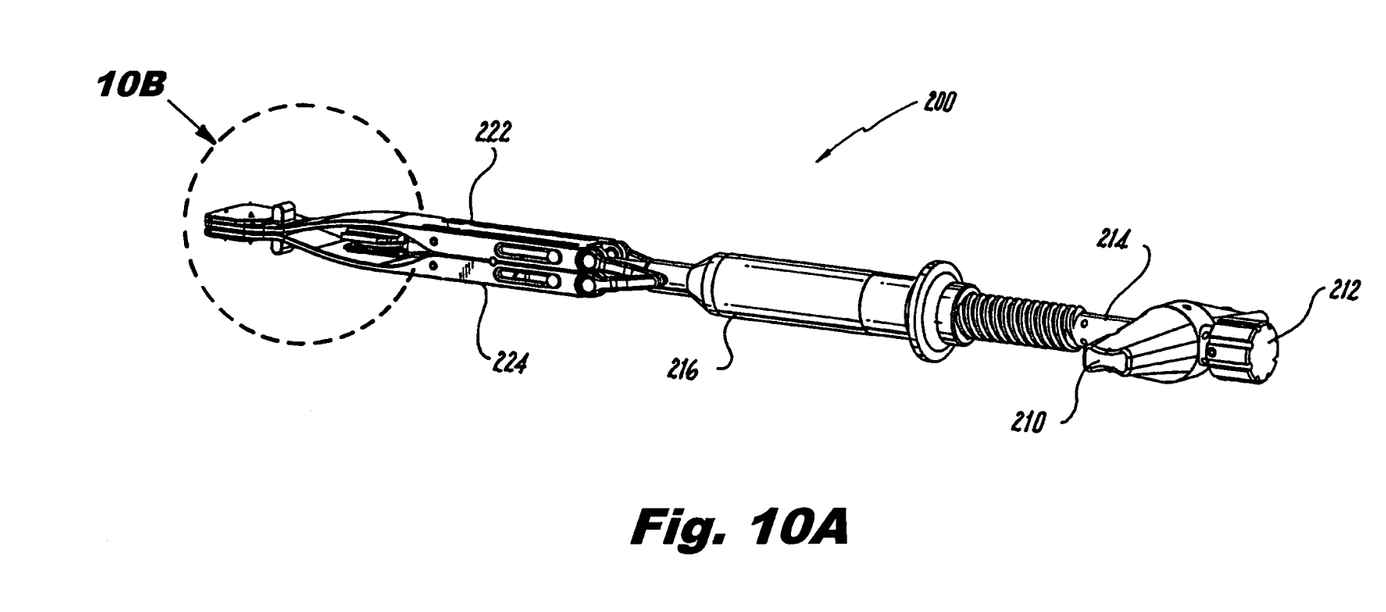
FIG. 10A is a perspective view of a distraction instrument coupled with the artificial disc replacement device of FIG. 1.
Figure 10B:
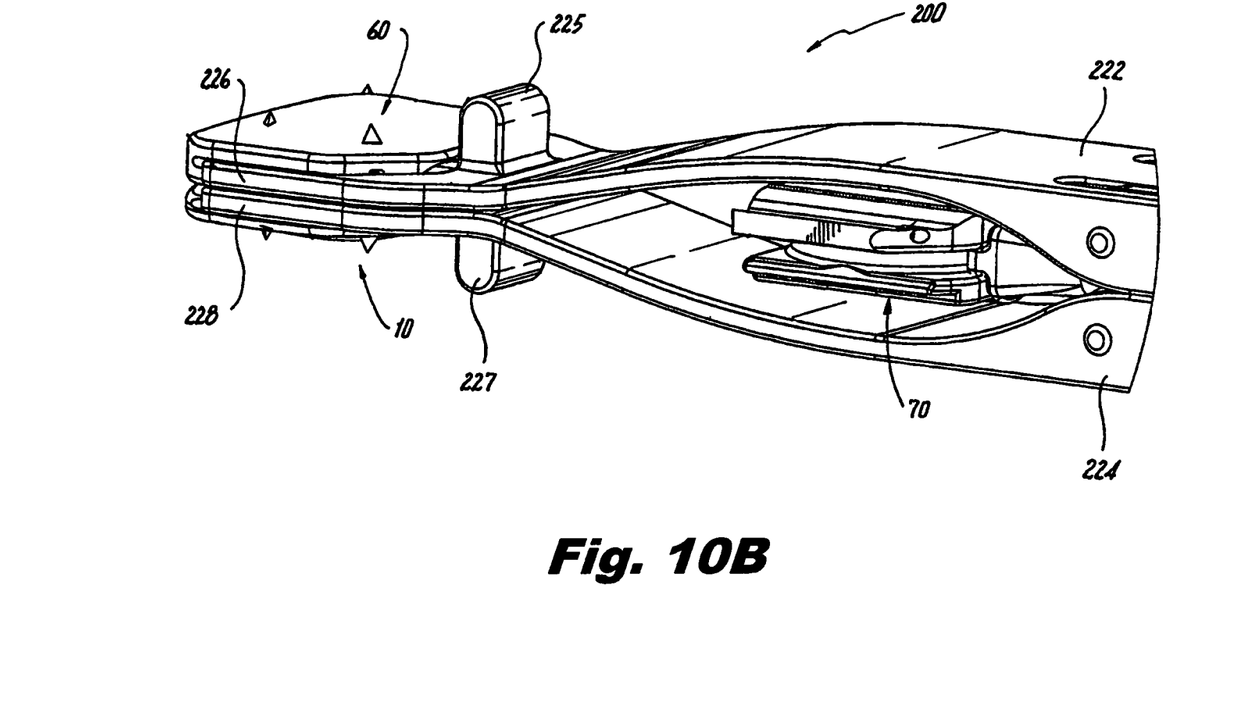
FIG. 10B is an enlarged perspective view of a distal end of the distraction instrument of FIG. 10A with the artificial disc replacement device of FIG. 1 coupled to a jaw assembly of the distraction instrument.
Figure 10C:
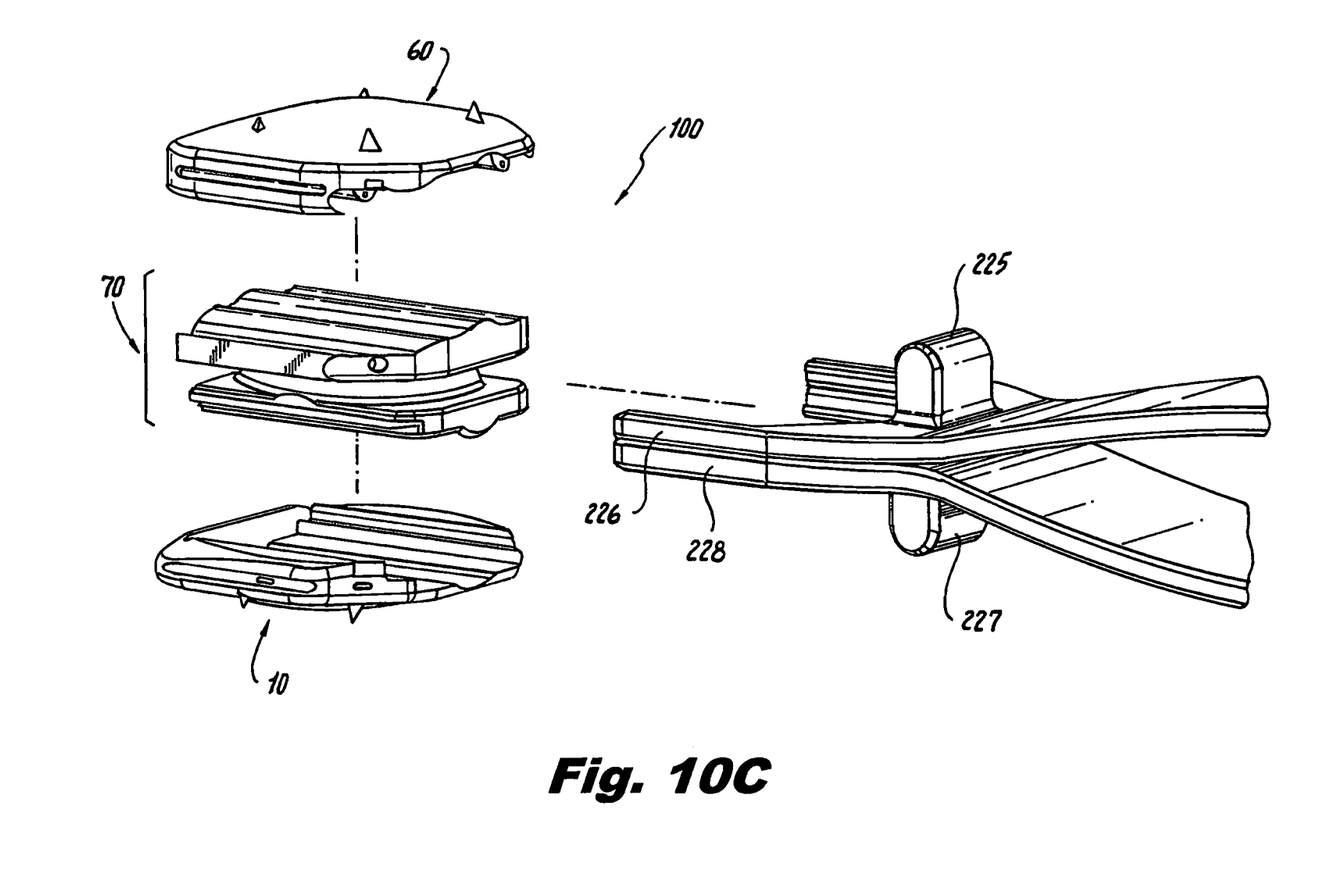
FIG. 10C is an enlarged view of the distal end of FIG. 10B with the jaws in a closed position and an exploded perspective view of the artificial disc replacement device of FIG. 1.

An installation tool 200 is shown in FIGS. 10A and 10B. The installation tool 200 includes a handle 210 and a knob 212. A partially threaded shaft 214 is threadably engaged with a housing 216. The threaded engagement between the shaft 214 and the housing 216 allows the shaft 214 to move longitudinally relative to the housing 216 in response to rotation of the handle 210. At the distal end of the shaft 214 is an attachment portion 218 that releasably couples the pivoting assembly 70 to the installation tool 200. The installation tool 200 also includes opposing arms 222, 224 that have blade or jaw portions 226, 228 extending distally therefrom. Each blade portion 226, 228 is generally U-shaped and is further configured and adapted for releasably engaging respective first and second plate members 10, 60. Each blade portion 226, 228 includes respective stop portions 225, 227 that limit the insertion depth of the blade portions 226, 228 between the adjacent vertebral bodies. Rotating the handle 210 in a first direction causes distal translation of the shaft 214 relative to the housing 216. As the shaft 214 advances distally, the pivoting assembly 70 engages inner surfaces of the blade portions 226, 228 urging them apart. When the pivoting assembly 70 is completely disposed between the first and second plate members 10, 60, the shaft 214 is at its distalmost position.

The disk 100 is installed between adjacent vertebral bodies using the installation tool 200. With the first and second plate members 10, 60 attached to respective blade portions 228, 226 and the pivoting assembly 70 releasably coupled to the attachment portion 218, the physician inserts the distal end of the installation tool 200 between the adjacent vertebral bodies until the stop portions 225, 227 engage the exterior of the adjacent vertebral bodies indicating that the maximum insertion depth has been achieved. Subsequently, handle 210 is rotated in a first direction and advances shaft 214 distally, thereby advancing the pivoting assembly 70 distally. During the distal movement of the pivoting assembly 70, the engaging member 50 and the support member 20 slidably engage inner surfaces of the blade portions 226, 228 urging them apart and distracting the adjacent vertebral bodies. Continued distal translation of the pivoting assembly 70 positions the pivoting assembly 70 between the first and second plate members 10, 60 such that the support member 20 and the engaging member 50 are attached to the first and second plate members 10, 60. Once the pivoting assembly 70 is attached to the first and second plate members 10, 60, the knob 212 is rotated so that the pivoting assembly 70 separates from the attachment portion 218 of the shaft 214. Subsequently, the installation tool 200 is removed. Since the first and second plate members 10, 60 are installed prior to any distraction of the adjacent vertebral bodies, inserting the pivoting assembly 70 between the first and second plate members 10, 60 requires a minimal amount of insertion force. As such, this reduces trauma to the patient and reduces deformation of the disk 100.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Thus the scope of the embodiments should be determined by the appended claims and their legal equivalents, rather than by the examples given.

What is claimed is:

1. An intervertebral implant comprising:
a first plate member having a bone engaging surface for engaging a first vertebral body;
a second plate member having a bone engaging surface for engaging a second vertebral body; and
a pivoting assembly disposed between the first plate member and the second plate member, the pivoting assembly adapted to enable the first plate member to pivot relative to the second plate member about a first axis extending through the pivoting assembly and inhibiting the first plate member from rotating relative to the second plate member about a second axis that is transverse to the first axis, the pivoting assembly including a cup sandwiched between a coupling member and a support member, wherein the cup, the coupling member, and the support member are separately stackable components of the pivoting assembly that cooperate to enable relative movement between the first and second plate members when stacked together between the first and second plate members, the support member having a substantially hemispherical dome and a pair of opposing arms extending therefrom, the cup having a complementary substantially hemispherical configuration and a pair of opposed openings configured to slidably engage the pair of opposing arms such that the cup is movable relative to the support member in a first direction and is inhibited from moving relative to the support member in a second direction that is orthogonal to the first direction.

2. The intervertebral implant of claim 1, wherein the bone engaging surfaces of the first plate member and the second plate member are adapted for engaging opposing vertebral endplates of the first and second vertebral bodies.

3. The intervertebral implant of claim 2, wherein the first and second plate members include a plurality of extensions, each extension adapted to frictionally engage one of the opposing vertebral endplates of the first and second vertebral bodies.

4. The intervertebral implant of claim 1, further including at least one engaging member for attaching the pivoting assembly to at least one of the first and second plate members.

5. The implant of claim 4, wherein the at least one engaging member includes wings that are slidably engageable with a recess defined by the second plate member.

6. The implant of claim 1, wherein each of the cup, the coupling member, and the support member is substantially coaxially aligned with a central axis extending between the first and second plate members when the pivoting assembly is positioned between the first and second plate members.

7. The implant of claim 1, wherein the pivoting assembly is separate from the first and second plate members.

8. An intervertebral implant comprising:
a first plate member having a bone engaging surface for engaging a first vertebral body;

a second plate member having a bone engaging surface for engaging a second vertebral body; and a pivoting assembly disposed between the first plate member and the second plate member, the pivoting assembly adapted to enable the first plate member to pivot relative to the second plate member about a first axis extending through the pivoting assembly and inhibiting the first plate member from rotating relative to the second plate member about a second axis that is transverse to the first axis, the pivoting assembly including a cup sandwiched between a coupling member and a support member, wherein the cup, the coupling member, and the support member are separately stackable components of the pivoting assembly that cooperate to enable relative movement between the first and second plate members when stacked together between the first and second plate members, the support member having a substantially asymmetric dome and a pair of opposing arms extending therefrom, the cup having a complementary substantially asymmetric configuration and a pair of opposed openings configured to slidably engage the pair of opposing arms such that the cup is movable relative to the support member in a first direction and is inhibited from moving relative to the support member in a second direction that is orthogonal to the first direction.

9. The intervertebral implant of claim 8, wherein the bone engaging surfaces of the first plate member and the second plate member are adapted for engaging opposing vertebral endplates of the first and second vertebral bodies.

10. The intervertebral implant of claim 9, wherein the first and second plate members include a plurality of extensions, each extension adapted to frictionally engage one of the opposing vertebral endplates of the first and second vertebral bodies.

11. The intervertebral implant of claim 8, further including at least one engaging member for attaching the pivoting assembly to at least one of the first and second plate members.

12. The implant of claim 11, wherein the at least one engaging member includes wings that are slidably engageable with a recess defined by the second plate member.

13. The implant of claim 8, wherein each of the cup, the coupling member, and the support member is substantially coaxially aligned with a central axis extending between the first and second plate members when the pivoting assembly is positioned between the first and second plate members.

14. The implant of claim 8, wherein the pivoting assembly is separate from the first and second plate members.

15. A method of installing an intervertebral implant comprising:
providing a distraction device having a jaw assembly with a pair of movable blades;
attaching a first plate member to one of the movable blades and a second plate member to the other of the movable blades;
inserting the first plate member and the second plate member attached to the distraction device between adjacent vertebral bodies;
operating the distraction device to spread apart the adjacent vertebral bodies with the first plate member in contact with one vertebral body and the second plate member in contact with the other vertebral body;
inserting a pivoting assembly including a cup, a coupling member, and a support member into a space between the first plate member and the second plate member, each of the cup, the coupling member, and the support member being separately stackable components of the pivoting assembly, wherein inserting the pivoting assembly includes rotatably engaging the support member and the cup, wherein the support member includes a substantially hemispherical surface with a pair of opposing arms extending therefrom and the cup includes a complementary configuration with a pair of opposed openings that are adapted for rotatably engaging the arms;
forming the intervertebral implant by securing the pivoting assembly to the first plate member and the second plate member to enable relative movement between the first and second plate members; and
removing the distraction device such that the first plate member and the second plate member engage opposing sides of the coupling and the coupling.

16. The method of claim 15, wherein inserting the pivoting assembly includes sandwiching the cup between the coupling member and the support member such that the cup is movable relative to the support member in a first direction and inhibited from moving relative to the support member in a second direction.

17. A method of installing an intervertebral implant comprising:
providing a distraction device having a jaw assembly with a pair of movable blades;
attaching a first plate member to one of the movable blades and a second plate member to the other of the movable blades;
inserting the first plate member and the second plate member attached to the distraction device between adjacent vertebral bodies;
operating the distraction device to spread apart the adjacent vertebral bodies with the first plate member in contact with one vertebral body and the second plate member in contact with the other vertebral body;
inserting a pivoting assembly including a cup, a coupling member, and a support member into a space between the first plate member and the second plate member, each of the cup, the coupling member, and the support member being separately stackable components of the pivoting assembly, wherein inserting the pivoting assembly includes rotatably engaging the support member and the cup, wherein the support member includes a substantially asymmetric surface with a pair of opposing arms extending therefrom and the cup includes a complementary configuration with a pair of opposed openings that are adapted for rotatably engaging the arms;
forming the intervertebral implant by securing the pivoting assembly to the first plate member and the second plate member to enable relative movement between the first and second plate members; and
removing the distraction device such that the first plate member and the second plate member engage opposing sides of the coupling and the coupling.

18. The method of claim 17, wherein inserting the pivoting assembly includes sandwiching the cup between the coupling member and the support member such that the cup is movable relative to the support member in a first direction and inhibited from moving relative to the support member in a second direction.

19. An intervertebral implant comprising:
a first plate member having a bone engaging surface for engaging a first vertebral body;
a second plate member having a bone engaging surface for engaging a second vertebral body; and
a pivoting assembly disposed between the first plate member and the second plate member, the pivoting assembly adapted to enable the first plate member to pivot relative to the second plate member about a first axis extending through the pivoting assembly and inhibiting the first plate member from rotating relative to the second plate member about a second axis that is transverse to the first axis, the pivoting assembly including a cup sandwiched between a coupling member and a support member, wherein the cup, the coupling member, and the support member are separately stackable components of the pivoting assembly that cooperate to enable relative movement between the first and second plate members when stacked together between the first and second plate members, the support member including a dome disposed on a base portion, the dome having a generally spherical shape, the support member including opposing arms that are positioned on wing portions of the base portion, the wing portions being slidably engageable with an opening defined in the first plate member to securely fix the first plate member and the support member to one another.

20. The implant of claim 19, wherein the cup is a generally hemispherical structure with a pair of opposed openings that slidably engage the opposing arms of the support member such that the cup nests atop the support member with the openings resting atop the opposing arms of the support member, the cup and the dome being configured such that a gap is defined between a bottom lip of the cup and the base portion of the support member to enable the cup to pivot.

21. The implant of claim 20, wherein an extension is disposed on one end of the cup opposite to the bottom lip.

22. The implant of claim 21, wherein the coupling member has a curvate upper surface and central opening configured to receive the extension of the cup.

23. The intervertebral implant of claim 19, wherein the bone engaging surfaces of the first plate member and the second plate member are adapted for engaging opposing vertebral endplates of the first and second vertebral bodies.

24. The intervertebral implant of claim 23, wherein the first and second plate members include a plurality of extensions, each extension adapted to frictionally engage one of the opposing vertebral endplates of the first and second vertebral bodies.

25. The intervertebral implant of claim 19, further including at least one engaging member for attaching the pivoting assembly to at least one of the first and second plate members.

26. The implant of claim 25, wherein the at least one engaging member includes wings that are slidably engageable with a recess defined by the second plate member.

27. The implant of claim 19, wherein each of the cup, the coupling member, and the support member is substantially coaxially aligned with a central axis extending between the first and second plate members when the pivoting assembly is positioned between the first and second plate members.

28. The implant of claim 19, wherein the pivoting assembly is separate from the first and second plate members.

* * * * *